(12) United States Patent
Watson et al.

(10) Patent No.: US 7,766,877 B1
(45) Date of Patent: Aug. 3, 2010

(54) MEDICAL DEVICE AND A SET OF PARTS FOR THE ASSEMBLY THEREOF

(75) Inventors: Jeremy Paul Watson, Birkenherd (GB); James Patrick Scanlan, Bristol (GB); Max Roy Woolley, Britol (GB)

(73) Assignee: Coloplast A/S, Humlebaek (DK)

( * ) Notice: Subject to any disclaimer, the term of this patent is extended or adjusted under 35 U.S.C. 154(b) by 901 days.

(21) Appl. No.: 10/129,975

(22) PCT Filed: Nov. 24, 2000

(86) PCT No.: PCT/GB00/04486

§ 371 (c)(1),
(2), (4) Date: Feb. 3, 2003

(87) PCT Pub. No.: WO01/37915

PCT Pub. Date: May 31, 2001

(30) Foreign Application Priority Data

Nov. 25, 1999 (GB) .................................. 9927900.2

(51) Int. Cl.
*A61M 5/178* (2006.01)
*A61F 5/44* (2006.01)

(52) U.S. Cl. .................................. 604/167.03; 604/349

(58) Field of Classification Search .................. 604/264, 604/167.03, 523, 164.12, 342, 544, 349–352
See application file for complete search history.

(56) References Cited

U.S. PATENT DOCUMENTS

| | | | | | |
|---|---|---|---|---|---|
| 3,713,447 A | * | 1/1973 | Adair | ........................... | 604/105 |
| 4,944,732 A | * | 7/1990 | Russo | ........................ | 604/247 |
| 5,073,116 A | * | 12/1991 | Beck, Jr. | ....................... | 439/71 |
| 5,073,166 A | * | 12/1991 | Parks et al. | .................. | 604/175 |
| 5,352,182 A | * | 10/1994 | Kalb et al. | ..................... | 600/30 |
| 5,476,434 A | * | 12/1995 | Kalb et al. | ..................... | 600/30 |
| 5,483,976 A | * | 1/1996 | McLaughlin et al. | ......... | 128/885 |
| 5,549,657 A | * | 8/1996 | Stern et al. | ................... | 604/537 |
| 5,704,353 A | | 1/1998 | Kalb et al. | | |
| 5,707,357 A | * | 1/1998 | Mikhail et al. | ......... | 604/167.03 |
| 5,749,826 A | * | 5/1998 | Faulkner | ....................... | 600/29 |
| 5,865,802 A | | 2/1999 | Yoon et al. | | |

(Continued)

FOREIGN PATENT DOCUMENTS

CA 2213540 * 2/1999

(Continued)

OTHER PUBLICATIONS

HUX, Hungarian search report.

(Continued)

*Primary Examiner*—Kevin C Sirmons
*Assistant Examiner*—Andrew M Gilbert
(74) *Attorney, Agent, or Firm*—Coloplast Corp., Coloplast A/S; Daniel G. Chapik; Nicholas R. Baumann

(57) ABSTRACT

A set of parts for providing a medical device, including a lumen element adapted for mounting at a location on the skin of the patient, and a valve member. The lumen element and the valve member have releasable connection members such that, when the connection members are engaged, an assembled medical device is provided which is adapted for accessing an internal organ of a patient.

23 Claims, 18 Drawing Sheets

U.S. PATENT DOCUMENTS

| | | | |
|---|---|---|---|
| 5,871,471 A | | 2/1999 | Ryan et al. |
| 5,882,340 A | | 3/1999 | Yoon et al. |
| 5,904,670 A | * | 5/1999 | Schreiner .................... 604/523 |
| 5,989,230 A | * | 11/1999 | Frassica ...................... 604/264 |
| 6,979,322 B2 | * | 12/2005 | Chu et al. ................... 604/248 |
| 7,070,587 B2 | * | 7/2006 | Meier et al. ................. 604/533 |

FOREIGN PATENT DOCUMENTS

| | | |
|---|---|---|
| CN | 2078635 | 6/1991 |
| GB | 2 275 420 | 8/1994 |
| HU | 36386 | 9/1985 |
| HU | 38845 | 7/1986 |
| HU | 9600293 | 1/1998 |

OTHER PUBLICATIONS

CNX, Translation of office action.

* cited by examiner

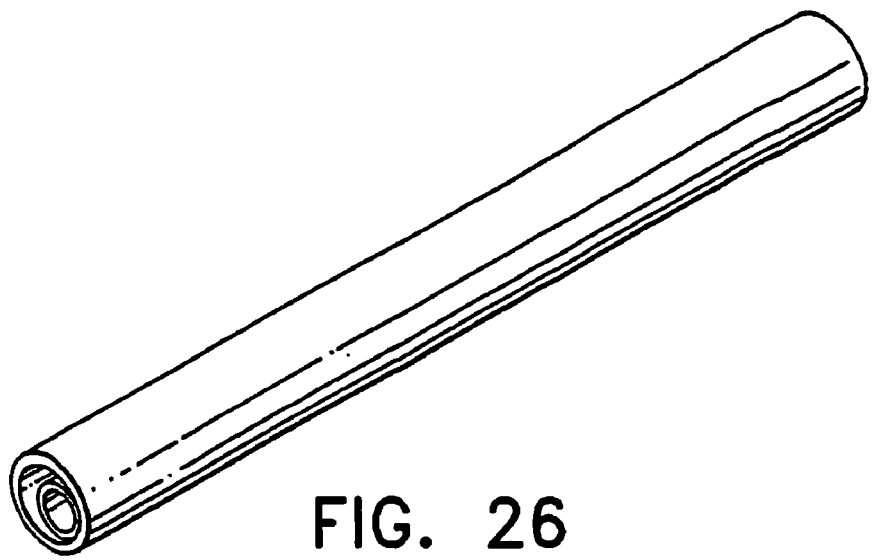
FIG. 26
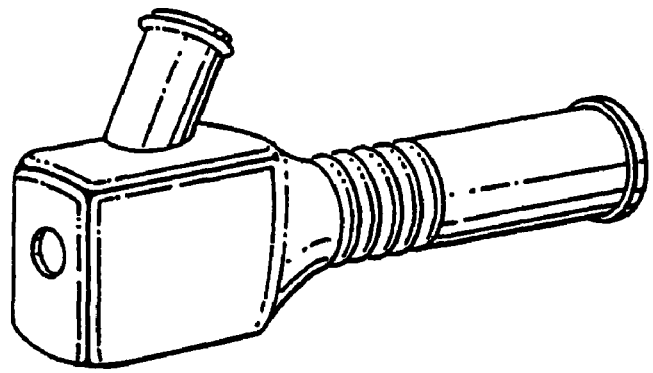
FIG. 27
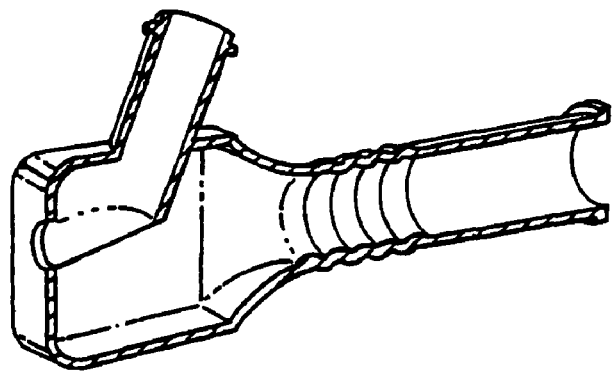

MEDICAL DEVICE AND A SET OF PARTS FOR THE ASSEMBLY THEREOF

BACKGROUND OF THE INVENTION

1. Field of the Invention

The invention relates to a medical device, and particularly to a set of parts for providing such a device.

2. Description of the Related Art

It is often necessary to provide a catheter for a patient. Moreover, it is also often necessary to provide for management of an internal organ of a patient, for example a bladder of a patient. In the past, catheters have been inserted through the urethra. It is also becoming good medical practice to introduce a catheter suprapubically. However, such catheters, generally those known as Foley catheters, cannot usually remain in situ for an extended period of time owing to blocking of the catheter resulting in the catheter having to be replaced, with attendant trauma for a patient.

It is accordingly an object of the invention to seek to mitigate this disadvantage.

SUMMARY OF THE INVENTION

According to a first aspect of the invention there is provided a set of parts for providing a medical device, comprising a lumen element adapted for mounting at a location on the skin of a patient, and a valve member, the lumen element and the valve member having releasable connection means, whereby when the means are engaged, an assembled medical device is provided which is adapted for accessing an internal organ of a patient.

Thus using the invention it is possible to avoid the use of a traditional Foley catheter and to use the said lumen element, which acts as a port installed on the patient's body skin, whereby to allow for both continuous or intermittent drainage of a body organ, to allow for irrigation of that body organ, and to allow internal investigation of the condition of the body organ and of the port itself by introduction of an instrument such as an endoscope through the lumen element.

The lumen element may comprise a lumen and a housing, and the housing may include the connection means of the lumen element. This provides for a relatively simple construction.

The housing and valve element may be releasably engaged by snap-engageable releasable connection means. This provides for a positive engagement, and a relatively simple construction.

The lumen of the lumen element may comprise a plurality of lumen. This provides for irrigation and drainage of a body organ such as a bladder.

There may be means adapted to retain the lumen element in a body organ. This provides for positive retention, and user comfort.

The retention means may comprise a deployable cage device, or alternatively a deployable petal device.

Again, the retention means may comprise a deployable finger device. All these devices can provide for positive retention in a body organ.

These constructions also avoid problems with traditional Foley catheters when the balloon thereof deflates prematurely or fails to deflate when required.

The deployable cage device may comprise a plurality of spaced elongate elements which in an undeployed mode may comprise part of the external surface of the lumen element, and in a deployed mode may extend laterally of that external surface.

The lumen element may be substantially of right circular cylindrical configuration, and the plurality of spaced elongate elements may comprise circumferentially spaced parts of the external surface of the lumen element.

The spaced elongate elements may be captive at each end, and may be flexible, the arrangement being such that when deployed the elements may be bowed externally of the external surface of the lumen element. This provides a relatively simple yet effective construction.

There may be a mechanism operable from the housing to deploy the retention means.

The deployment mechanism may comprise a pull means extending between a distal end of the lumen element and the housing. This is a relatively simple yet effective construction, particularly when the pull means may comprise a plurality of cords mounted circumferentially of the lumen element.

There may be means to pull the cords in a direction towards the housing.

The pull means may comprise a capstan device to which the cords may be connected, whereby on rotation of the device, the cords are drawn towards the housing. This provides for a positive pulling action which effectively "shortens" the cords to operate the retaining device.

There may be two diametrically disposed cords and the capstan device may comprise a rotatable member to which the cords are attached, and an abutment member over which the cords may pass when the rotatable member is rotated, the arrangement being effectively to shorten the cords and hence draw them towards the housing whereby to deploy the retention means.

There may be means to obviate flow of body fluids along the cords to the housing.

This provides for lowering the risk of contamination or cross-contamination as for example urine cannot pass from the interior to the exterior of the (assembled) medical device.

There may be a connector member adapted for releasable engagement with the valve member. This provides for adaptability of use of the medical device, particularly when there may be a plurality of separate connector members, each of which may be adapted for releasable engagement of the valve member.

Each connector member may also be operable to open a valve of the valve member on engagement therewith. This provides for a positive construction, and operation, and provides for automatic operating of the valve.

The connector members may comprise at least a catheter member, an endoscopic connection member, and a closure member. This provides for a versatile set of parts.

The connector members and valve member may comprise bayonet construction means. This provides for a relatively simple yet positive connection.

At least one connector element may comprise an internal concentric tube which is adapted to engage the valve, open it and seal against it.

There may be a zone of weakness in the material of the connector member at or adjacent a blind end of the bayonet connection means. This provides for release of the parts at a predetermined force, and thus avoid displacement or dislodgement of the port from an installed position, and has an additional advantage of avoiding damage to the set.

The zone of weakness may be defined by slots through the material of the connector element, or alternatively by a relatively thin portion of the material of the connector element.

There may be a dressing adapted to be mounted between the lumen element and the skin of the patient. This provides for comfort for a user, and avoidance of contamination.

The dressing may comprise a split ring of felt, lint, or polyurethane foam. This is a relatively simple yet effective construction.

According to a second aspect of the invention there is provided a medical device whenever assembled from a set as hereinbefore defined.

The device may comprise a bladder management device.

A set of parts for providing a medical device, and a device assembled therefrom, are hereinafter described, by way of example, with reference to the accompanying drawings.

BRIEF DESCRIPTION OF THE DRAWINGS

FIGS. 16 to 27 show schematically an actual set of parts according to the invention.

DETAILED DESCRIPTION OF THE PREFERRED EMBODIMENTS

Figure 1:
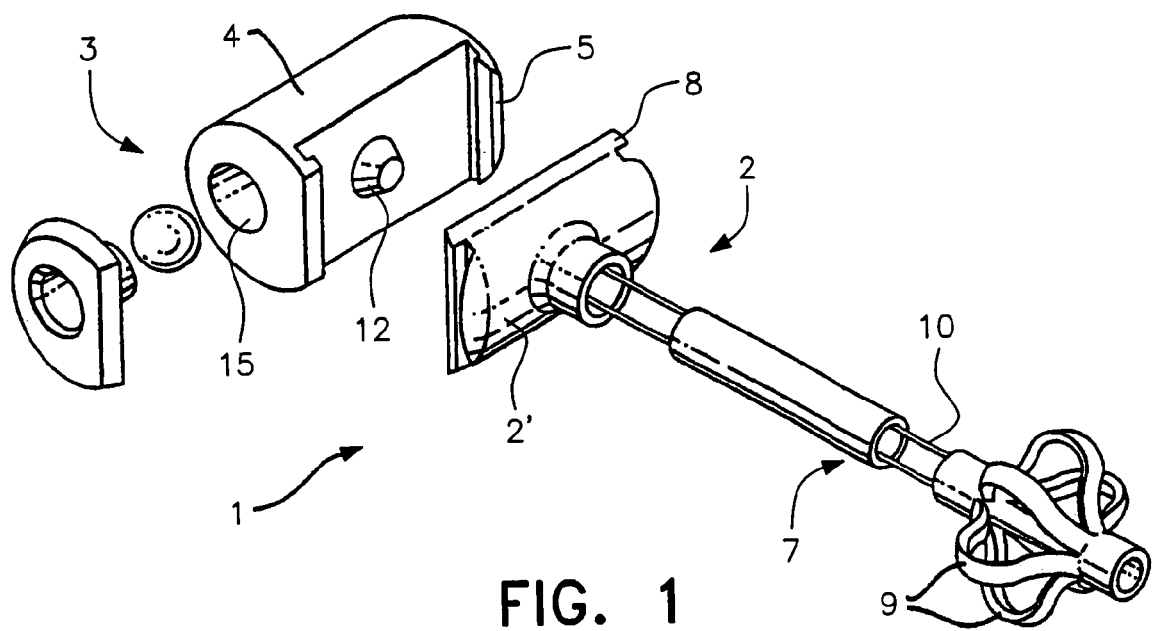
FIG. 1 is a schematic perspective view of a set of parts for providing a medical device, according to the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Referring to the drawings, in which like parts are referred to by like reference numerals, there is shown a set of parts 1 for providing a medical device such as a device for irrigating or catheterising a bladder of a patient using a catheter (not shown). There is a lumen element 2 which is adapted to be mounted on the body of the patient by being mounted on the patient's skin, by being essentially an implant. There is a valve member 3 of the set 1 of parts which has a body or housing 4 incorporating a valve 6 (FIG. 2) which is operable to allow passage therethrough to the lumen element 2, there being respective releasable connection or engagement members 5, 8 of the valve member and lumen element, respectively, which enable the valve member 3 to bereleasably mountable on the lumen element 2.

The releasable engagement members 5, 8 comprise in the embodiments snap engageable means at the sides of the respective lumen element and valve member. The lumen element 2 has a housing 2' for its engagement member 8 and a depending lumen 7 for entry into the body of a patient from the skin and thence into a body organ or cavity such as a bladder. The distal end of the lumen, which is a double lumen, has retaining means 9 in the form in the embodiment shown in FIG. 1 of longitudinally extending separate external boundary surface parts.

There are flexible pull cords, wires, sutures or strings 10 extending to the housing 2' of the lumen element 2 from the distal end thereof where they are secured so that when pulled and essentially "shortened" by any suitable means such as a capstan device 11 (FIG. 11) located in the housing, the distal end of the lumen 7 is drawn towards the housing. The only way this can be accommodated is by the elements 9 bowing outwardly as shown in FIG. 1, thereby providing an obstacle to withdrawal of the lumen from, for example, the bladder of a patient as the expanded elements 9 form a cage which has a lateral extent greater than the diameter of the entrance to the bladder. There are two cords 10, which are diametrically disposed in relation to the lumen. There may be means to obviate passage of urine along the cords from the distal end to the skin of the patient.

The lumen element housing 2' has a complementary-shaped seating for an outlet 12 from the valve member, providing a fluid tightseal, and the valve member 3 has a port 13 for connection of an outlet for urine, for example, and an entry port 15 shown in FIG. 1 for a catheter or for an irrigant for irrigating a bladder of a patient.

The lumen element housing 2' has a complementary-shaped seating for an outlet 12 from the valve member, providing a fluid tight seal, and the valve member 3 has a port 13 for connection of an outlet for say urine and an entry port shown in FIG. 1 for a catheter or for an irrigant for irrigating a bladder of a patient.

The set of parts 1 includes also at least a catheter such as a Foley catheter, and connector members such as an endoscope (not shown) and a closure cap 14.

When the lumen element 2 is in place, implanted essentially at the skin of a patient, above the pubic area and thereby forming a suprapubic support, a catheter can be inserted through the valve member 3, and lumen element 2 down one bore of the lumen 7 into the bladder of the patient for passage of urine etc. along the other bore of the lumen 7 to the outlet port 13 of the valve member, the valve being automatically opened when the catheter is inserted.

When the valve member 3 is removed from the lumen element 2, an endoscope can be inserted through the housing thereof into the lumen and therealong so that an internal visual investigation can be carried out in situ in the bladder.

The closure cap 14 can be applied to the lumen housing when the set is not being used for catheterisation or endoscopy, the cap 14 being snap-engageable on the lumen housing not only to provide for a hygienic closure, but also to provide an aesthetic closure.

There may be a dressing such as a split ring of felt, lint, or polyurethane foam which can be replaceable and which can be positioned between the housing 2' and skin of the patient around the top of the lumen 7. This acts as a swab for any body fluid at the skin entry and as a cushion.

The basic set described hereinbefore is shown in FIG. 1.

Figure 2:
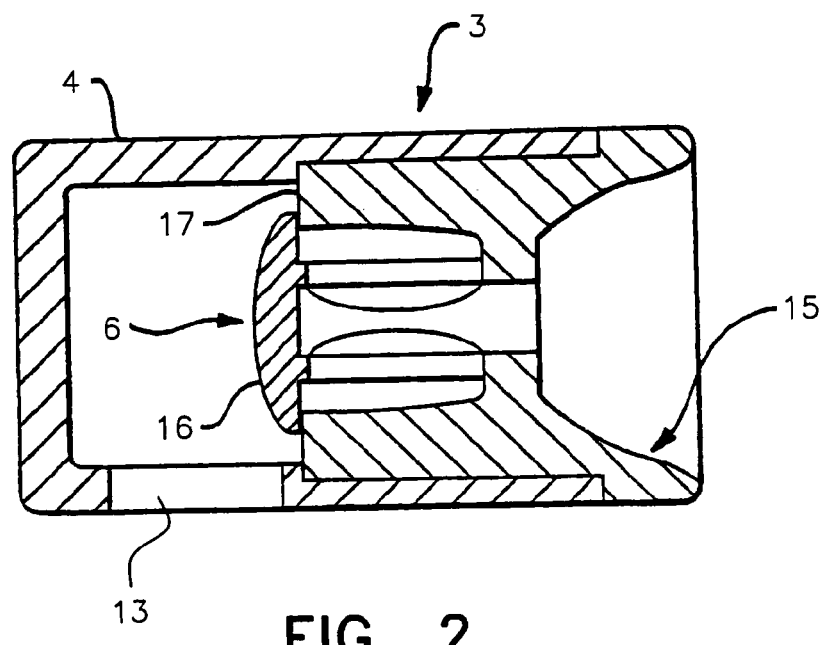
FIG. 2 shows a schematic view of a valve member of the set.

FIG. 2 shows schematically a valve member 3 which can act as an intermittent valve. There is a housing 4 with a mouth or entry 15 having a conical or flared mouth and the internal valve 6 which has a valve head 16 which can be lifted off a valve seat 17 on assembly with the lumen element for flow of urine through a port.

Figure 3:
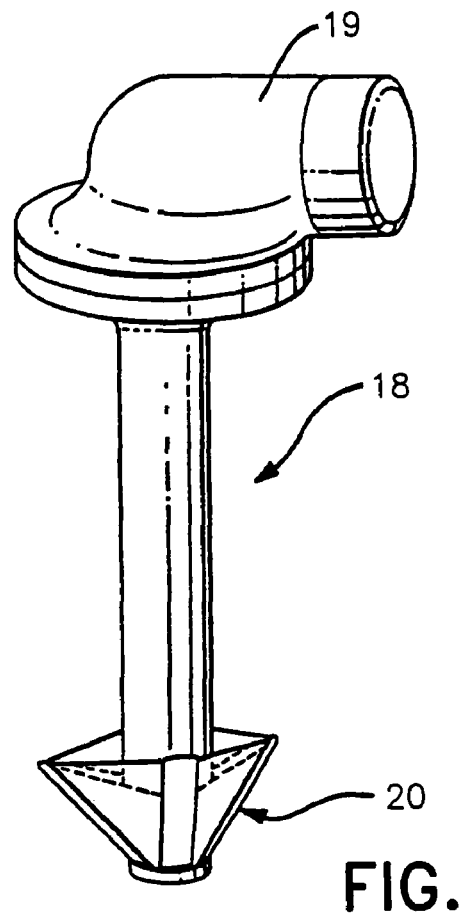
FIG. 3 shows an assembled set according to the invention.

FIG. 3 shows a further embodiment of a lumen element 18 and a valve member 19 assembled therewith, the lumen element having an umbrella-type retention means 20 which is shown deployed. The valve member 19 is shown disassembled in FIG. 4, there being a valve element 21 which is lifted from a valve seat on insertion of a tube in the port, and seals 22 to effect a fluid-tightseal with the lumen element.

Figure 4:
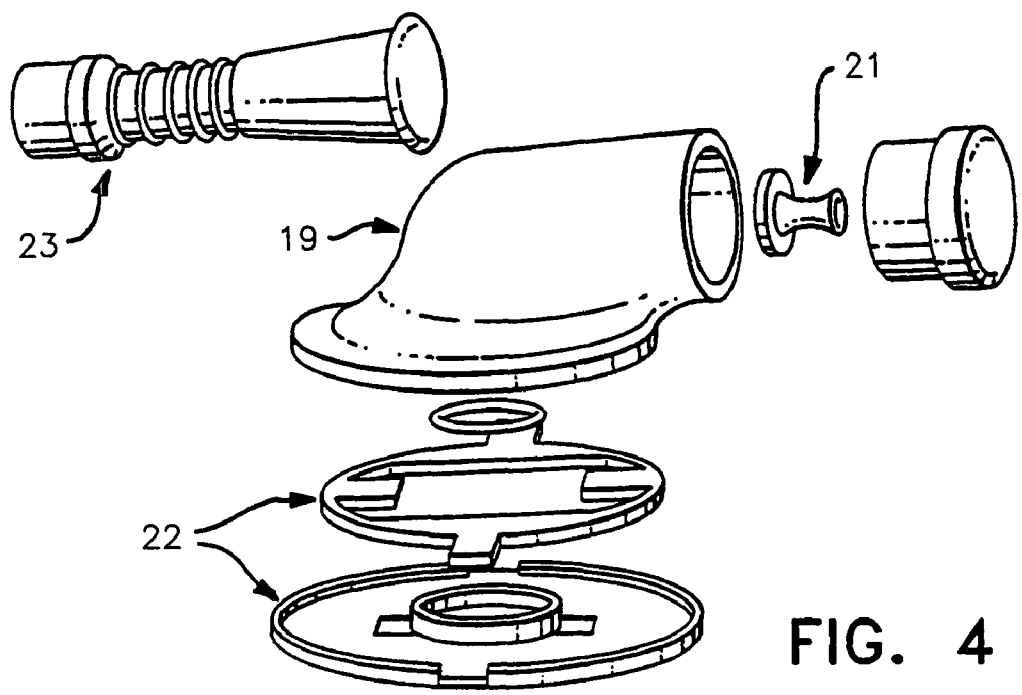
FIG. 4 shows an exploded view of a valve member.
Figure 5:
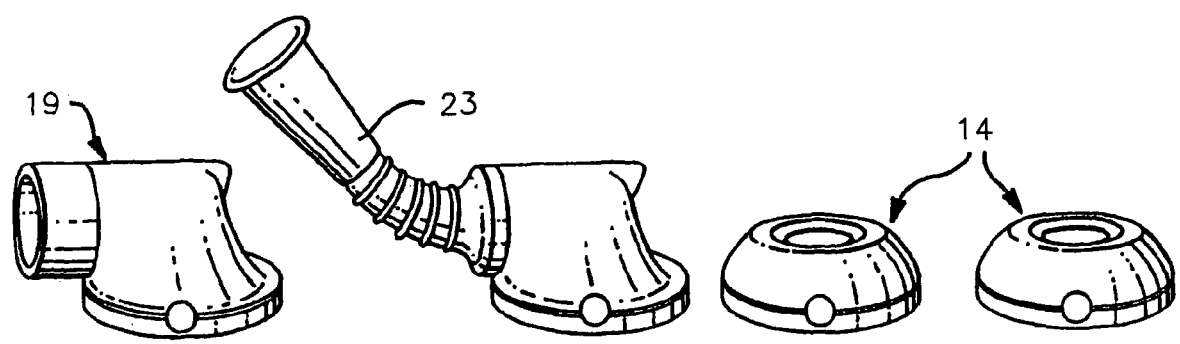
FIG. 5 shows various assemblies of valve member according to the invention.

FIG. 5 shows the valve member 19 of FIG. 4 assembled with an outlet tube 23, and covers or caps 14 for mounting on the lumen element.

Figure 6:
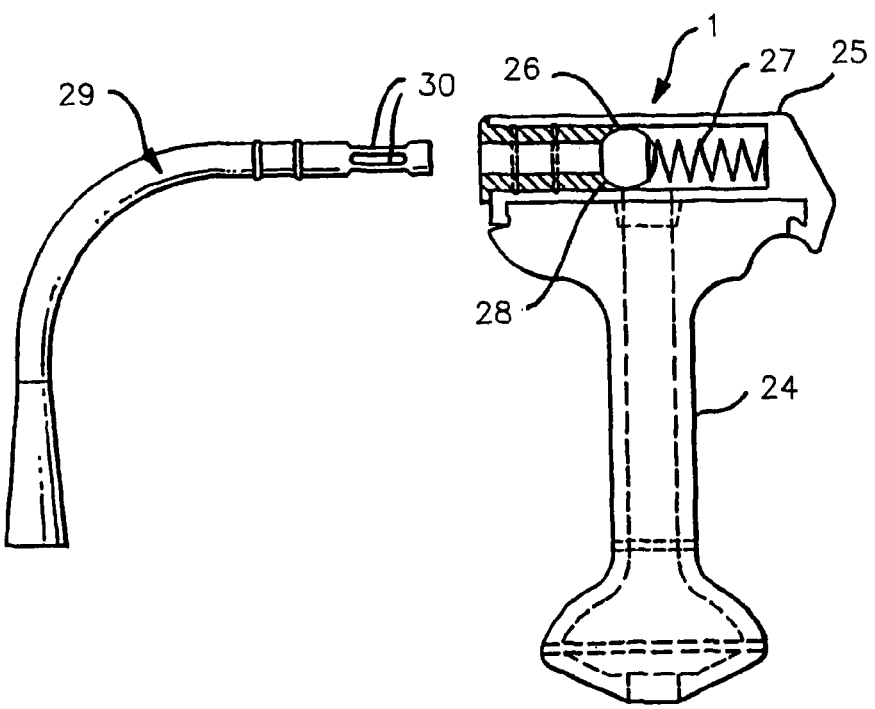
FIG. 6 shows an assembly of a further set according to the invention.
Figure 7:
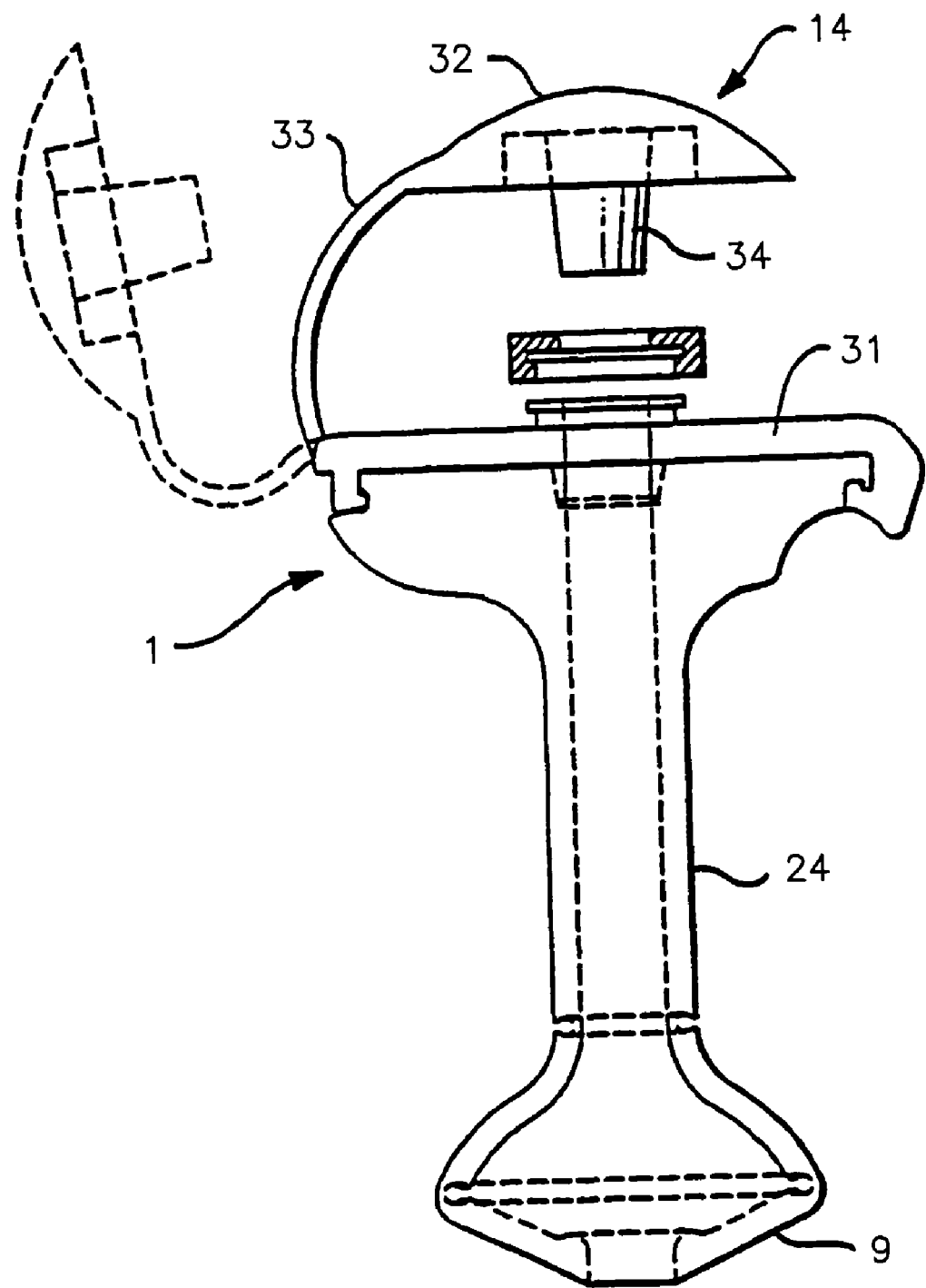
FIG. 7 shows a further assembly.
Figure 8:
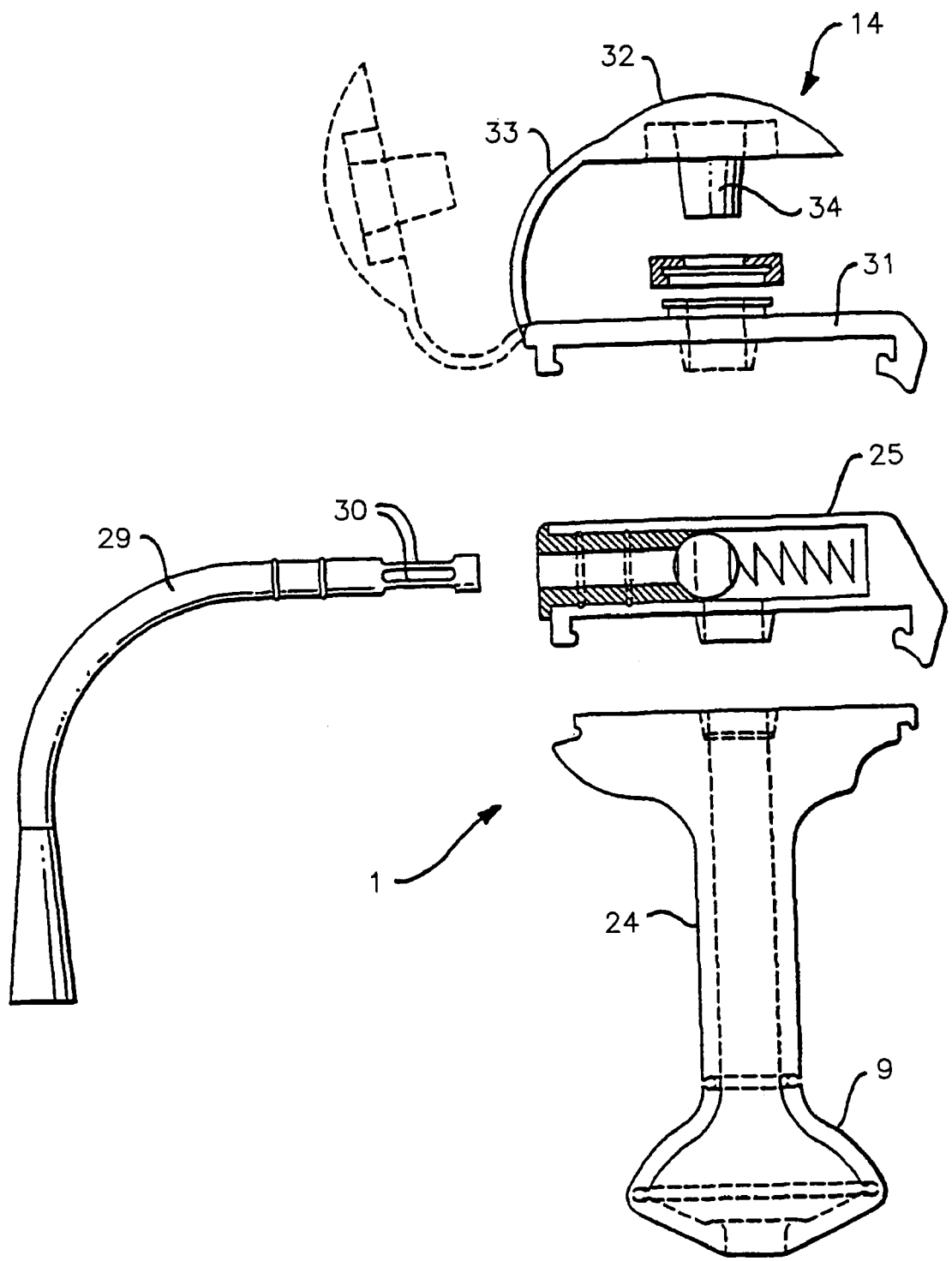
FIG. 8 shows an exploded view of the various components of FIGS. 6 and 7.

FIGS. 6, 7 and 8 show schematically further embodiments of a set of parts 1 embodying the invention.

In FIG. 6 there is shown a lumen element 24 with a valve member or drainage cap 25, releasably mounted thereon, the valve member 25 having in its housing a ball valve 26 biased by biasing means such as a spring 27 against a part spherical valve seat 28 to close off passage through the valve to the lumen element 24. When a drainage tube 29 is inserted in the valve member 25, an end thereof pushes the ball 26 off the seat 28 against pressure of the spring 27 to open a flow passage for urine along the lumen past the ball 26 and out of the tube 29 through inlet openings 30 thereto.

FIG. 7 shows a closure cap 14 of the set which can be applied when the valve member 25 is removed. The cap 14 has a mounting part 31 and a closure 32 which are connected together by a resilient connector 33, the cap 14 having a spigot or stopper 34 of frusto-conical configuration which is inserted in a similar shaped entry into the lumen element 24. When the cap 14 is in the dotted line position, an endoscope can be passed down the lumen. There is expansible retention means 9 as before.

FIG. 8 shows the lumen element, valve member and cap disassembled.

Figure 9B:
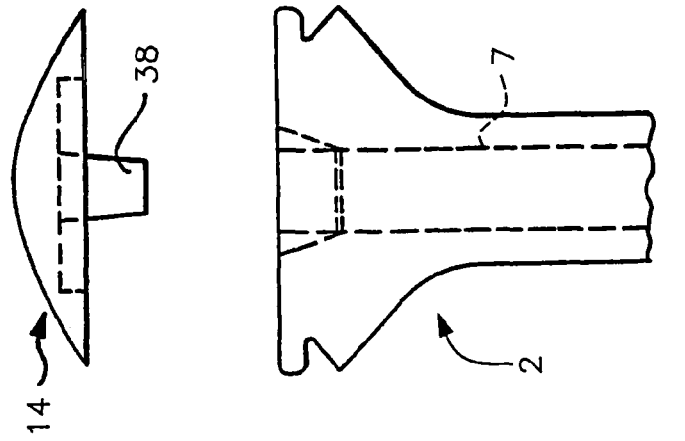
FIGS. 9, 9A and 9B show another embodiment of set according to the invention.
Figure 9A:
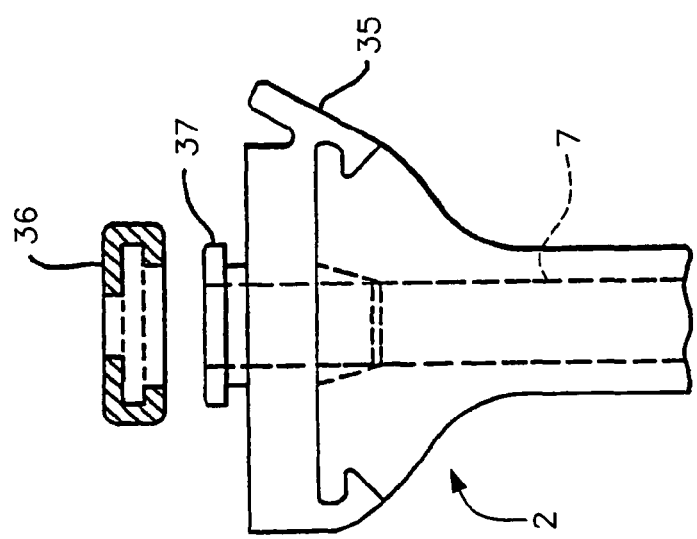
Figure 9:
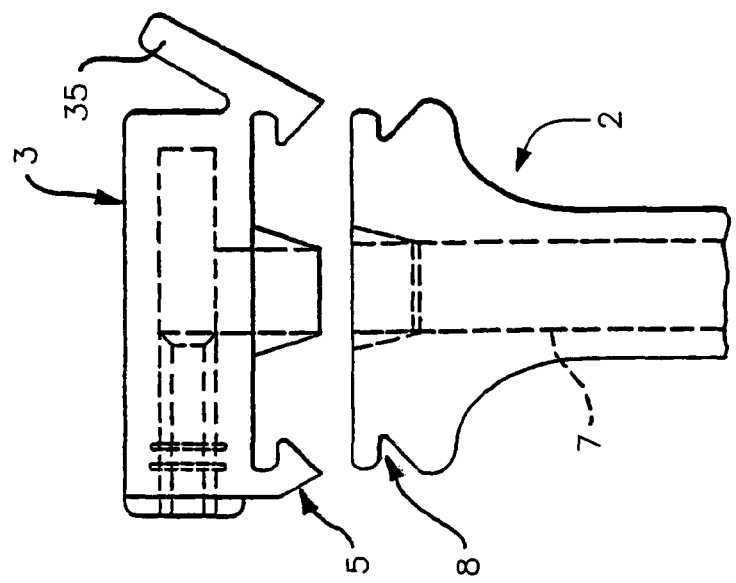

FIGS. 9 to 9B show further embodiments, there being a finger grip 35 which is angled to provide a means for disengaging the connection members 5, 8 of the valve member and lumen element 2, which are snap-engageable means as shown. In FIG. 9A there is shown an endoscopy and irrigation set part 36, in the form of an annular seal for seating round an entry 37 to an attachment for snap-engageable mounting on the lumen element.

FIG. 9B shows apush-engageable sealing cap 14 having a frustoconical spigot 38 for insertion into the lumen 7 of the lumen element 2.

Figure 10A:
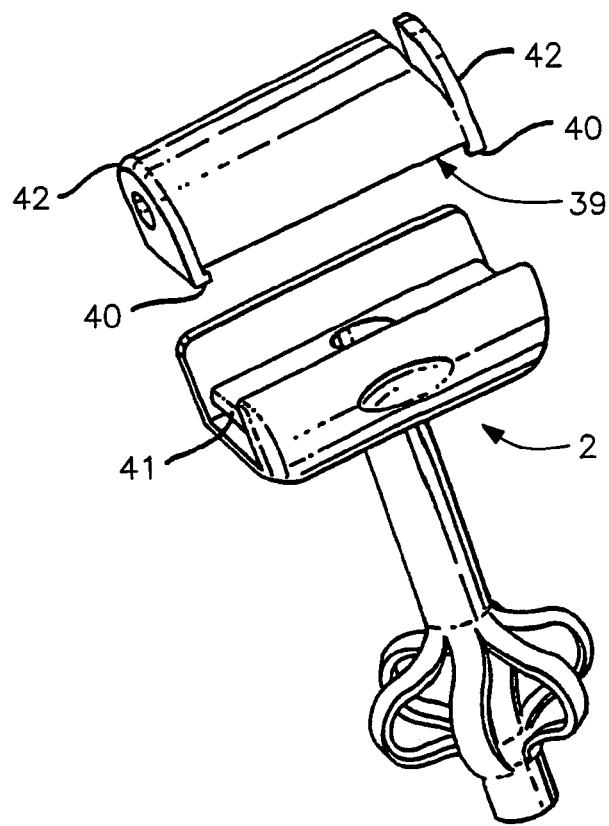
FIG. 10A shows a perspective exploded view of another embodiment of a set according to the invention.
Figure 10B:
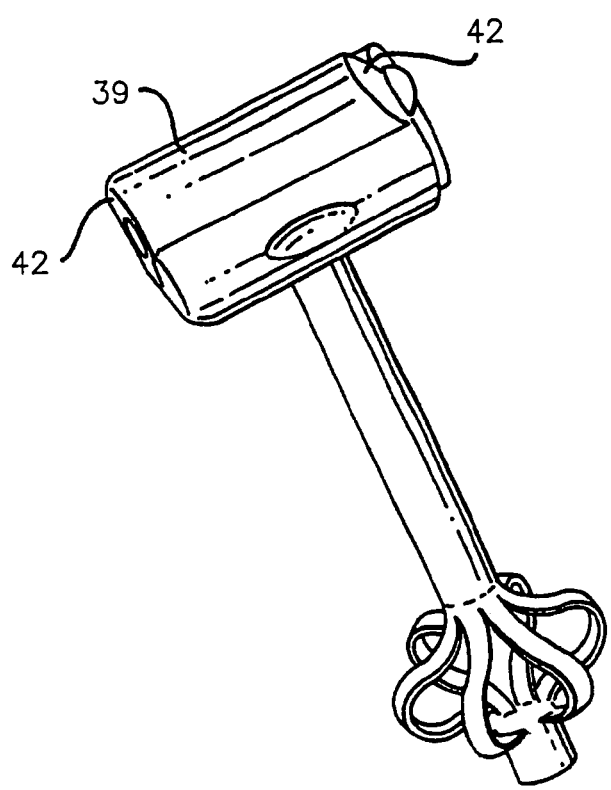
FIG. 10B shows the set of FIG. 10A, assembled.

FIGS. 10A and 10B show an embodiment similar to that of FIG. 1, a valve member 39 having a housing with lateral spring catch members 40 having hook-ends which engage with undercut lips or shoulders 41 of the lumen element 2 when the valve member 39 is offered up to and snap engaged with the lumen element. There are upstanding levers 42 which can be gripped and moved under finger pressure towards the housing of the valve member 39 to pivot the catch members 40 outwardly to release them from the lumen element for removal therefrom.

Figure 11:
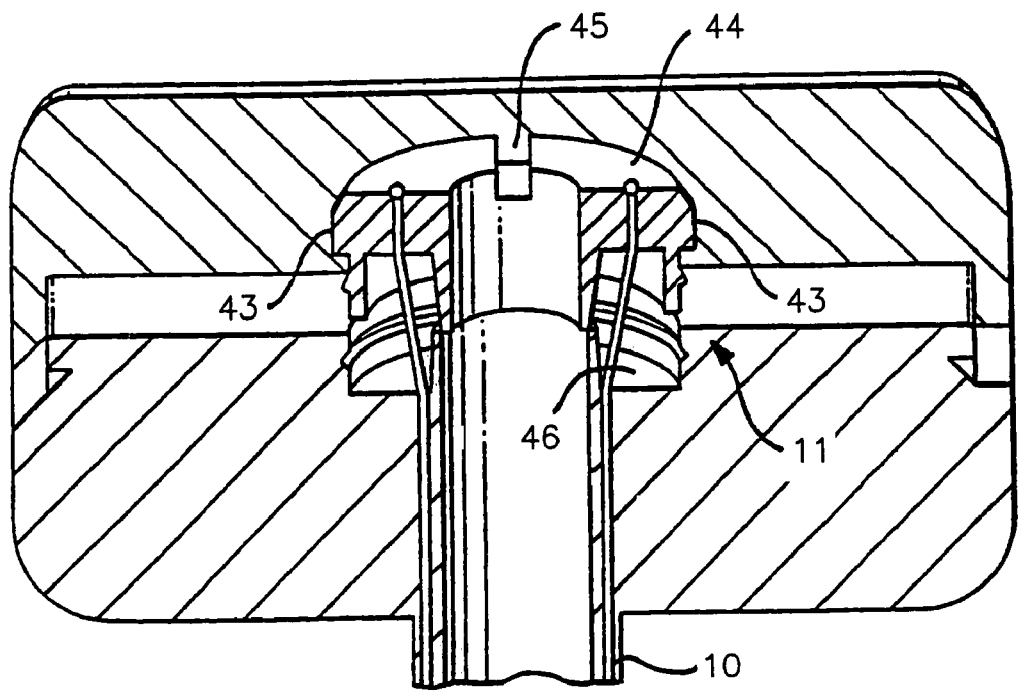
FIG. 11 shows a schematic view of actuating means for retaining means of the set.

FIG. 11 shows schematically the capstan or drum device 11 for retaining the two cords 10. and for drawing them in a direction to "shorten" them as described hereinbefore, whereby to deploy the retention means 9. The cords 10 are attached to lateral wings of a rotatable capstan-kind of member 44 which has a slot 45 in it for receiving a tool to turn it, thereby drawing the cords 10 over a curved (semi-circular) protrusion 46. As the cords pass thereover, they are effectively shortened and this is accommodated by the distal end of the lumen moving towards the lumen element housing, and thus deploying the lumen retaining means 9.

Figure 12A:
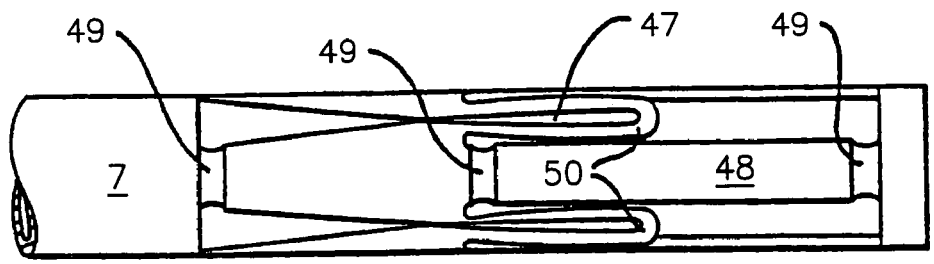
FIGS. 12 and 12A show separate side elevational views of retaining means according to the invention.
Figure 12B:
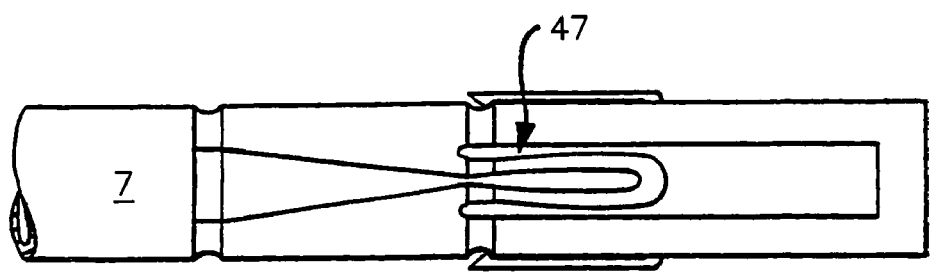

FIGS. 12A and 12B show an alternate embodiment of retention means 47 comprising elements 48 with a relatively thinner body parts 49 and integral folded over parts 50 forming spring elements. As the distal end of the lumen is drawn upwardly (to the left FIGS. 12A and 12B) the elements 48 flex about the body parts 49, to form a double conical retention means with the greatest diameter thereof being at the central part in the deployed position. To release the lumen from the bladder, the capstan device is rotated in the opposite direction to that for retention, and the elements 48 spring back to the position shown, so returning the longitudinal elements 48 to the position shown too, for withdrawal.

Figure 13A:
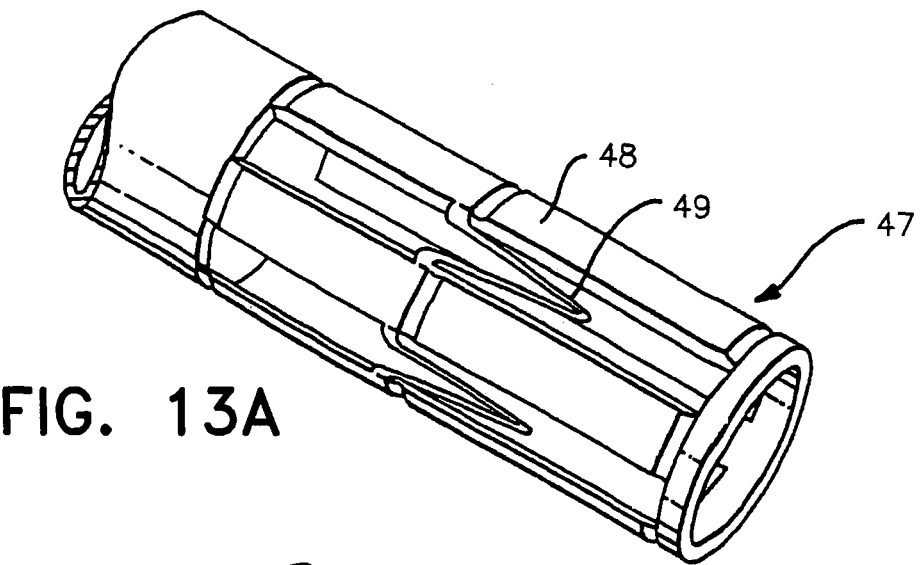
FIGS. 13A, 13B and 13C show views of alternative retaining means.
Figure 13B:
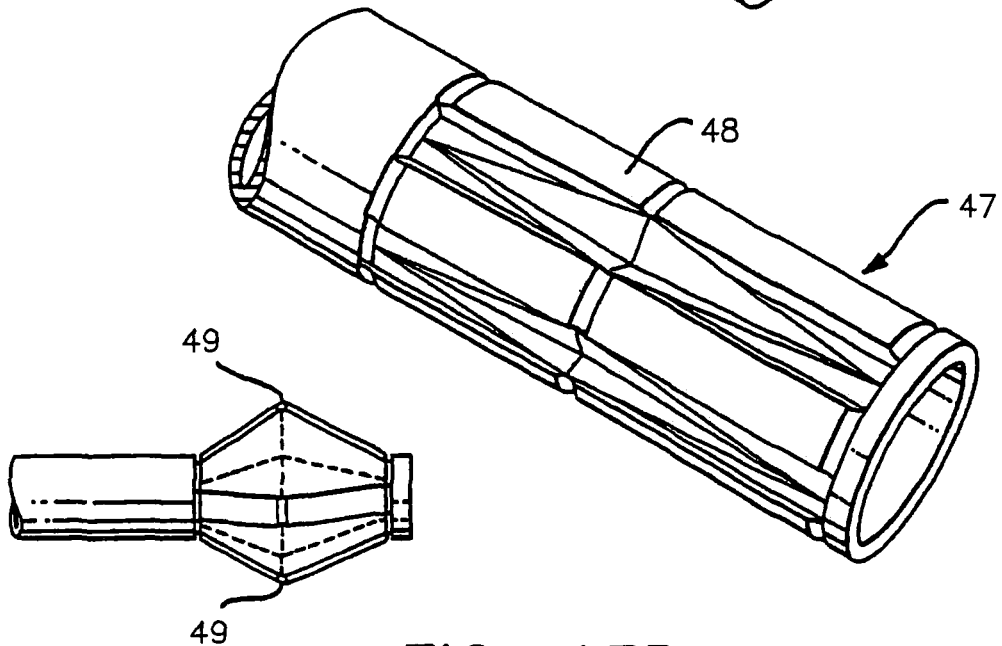
Figure 13C:
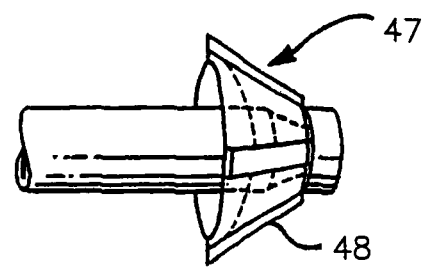
Figure 14B:
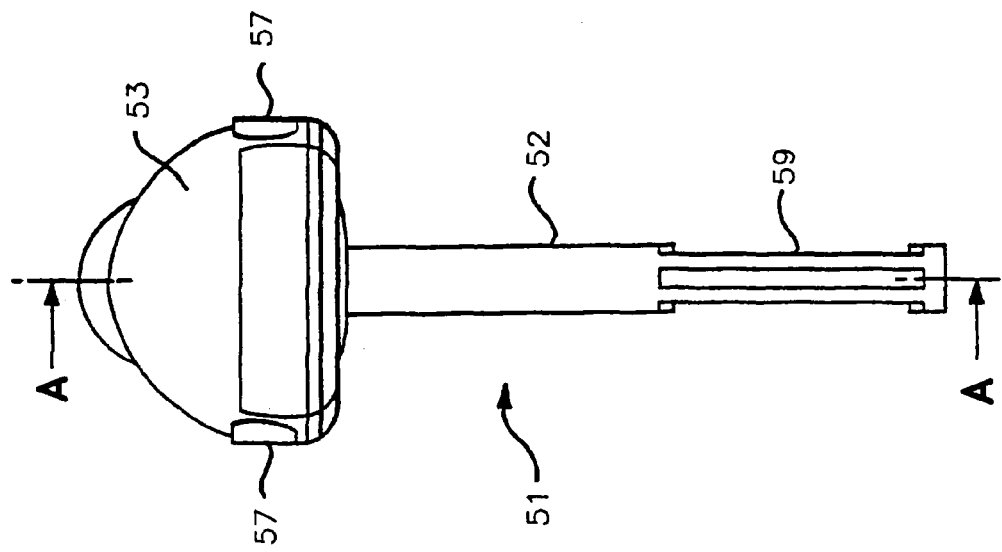
FIGS. 14A-14D show schematically a fourth embodiment, FIG. 14A being a longitudinal sectional view on line A-A of FIG. 14B, FIG. 14C being a side elevational view, and FIG. 14D being a perspective view.
Figure 14A:
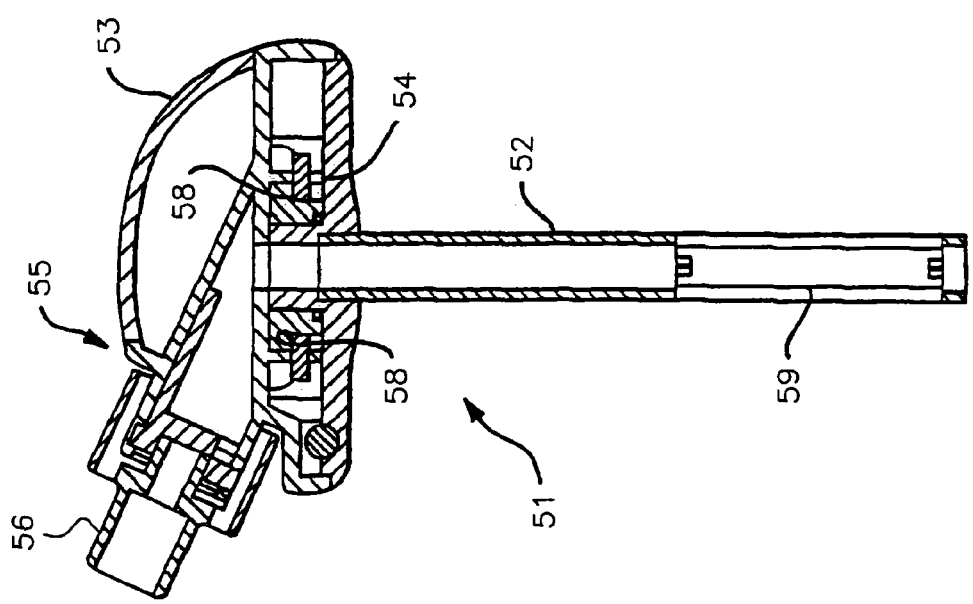
Figure 14D:
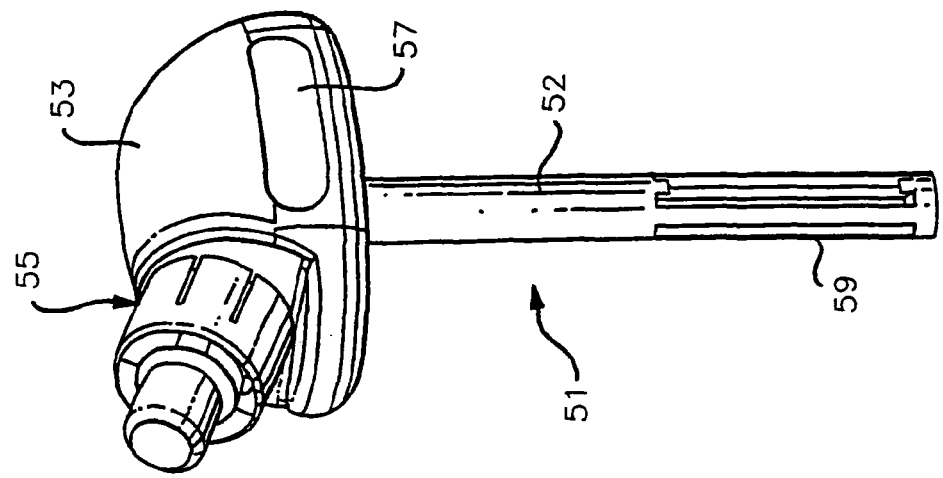
Figure 14C:
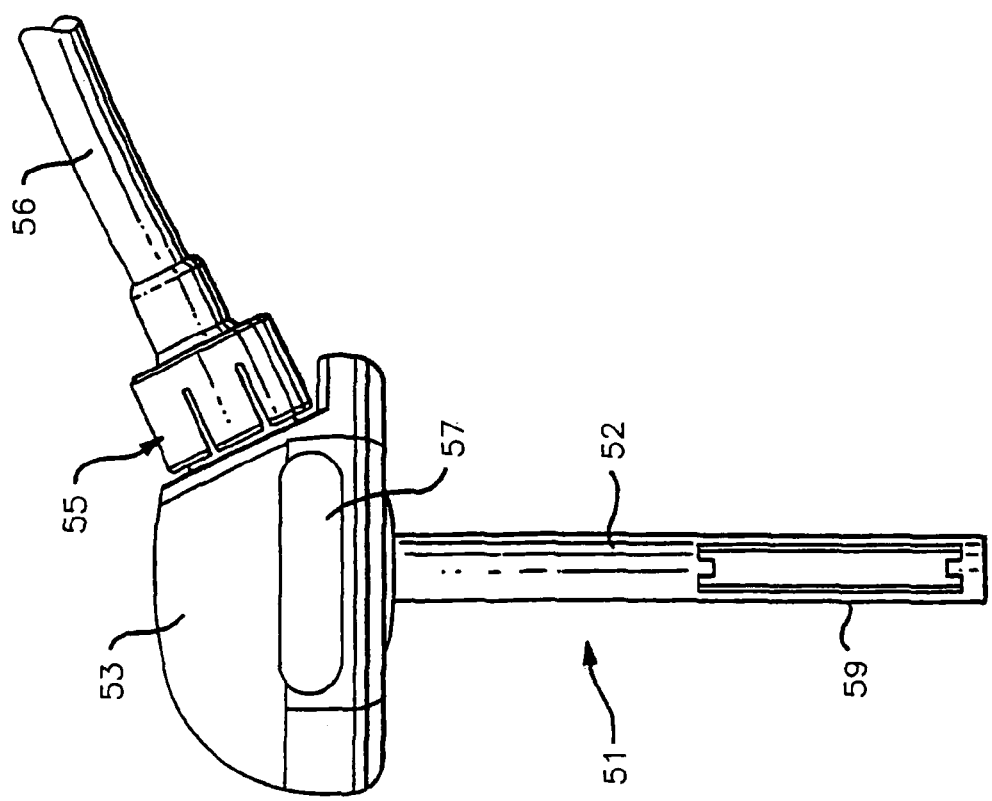

Similar arrangements are shown in FIGS. 13A to 13C, in FIG. 13C the retention means being like a petal.

Referring now to FIGS. 14A-14D, this embodiment of a set of parts 51 comprises a lumen element 52 for mounting on the skin of a patient and a valve member 53 which in the embodiment is a domed cap which is releasably mounted by snap-engaging members 54 on the lumen element 52 and has a port 55 for releasable attachment of catheter 56. The domed cap 53 has lateralhand-operable means 57 in the form of finger and thumbdepressible elements, which when pressed inwardly, that is "into" the body of the valve member, resilient teeth or catches comprising part of the engagement members 54 are flexed outwardly to disengage from under detents 58 so that the cap 53 can be removed, for replacement by a similar cap which can be a simple closure or end device, or a cap with a port for entry of a device such as an endoscope. As in the other embodiments described hereinbefore, there is retention means in the form of an expansible cage device 59.

Figure 15A:
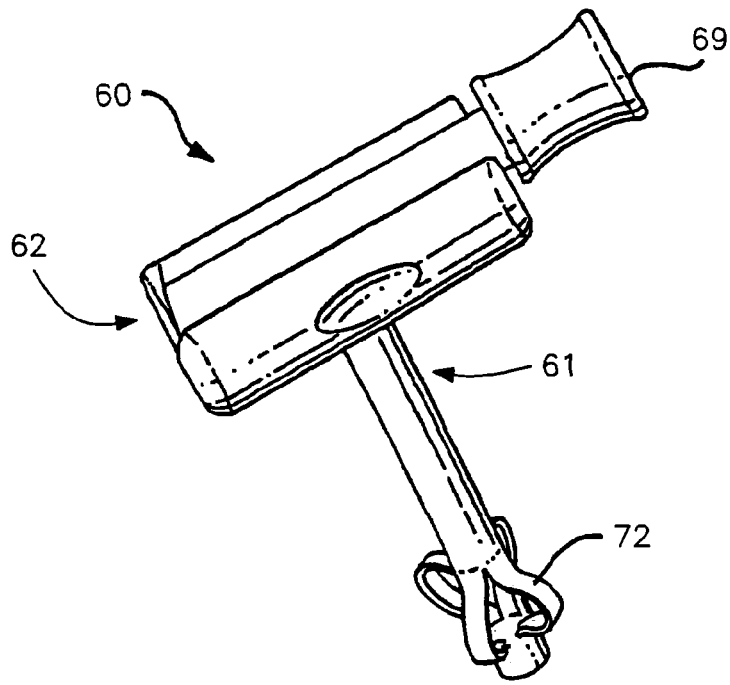
FIGS. 15A and 15B show respectively a perspective view of an actual embodiment and FIG. 15B a longitudinal sectional view thereof.
Figure 15B:
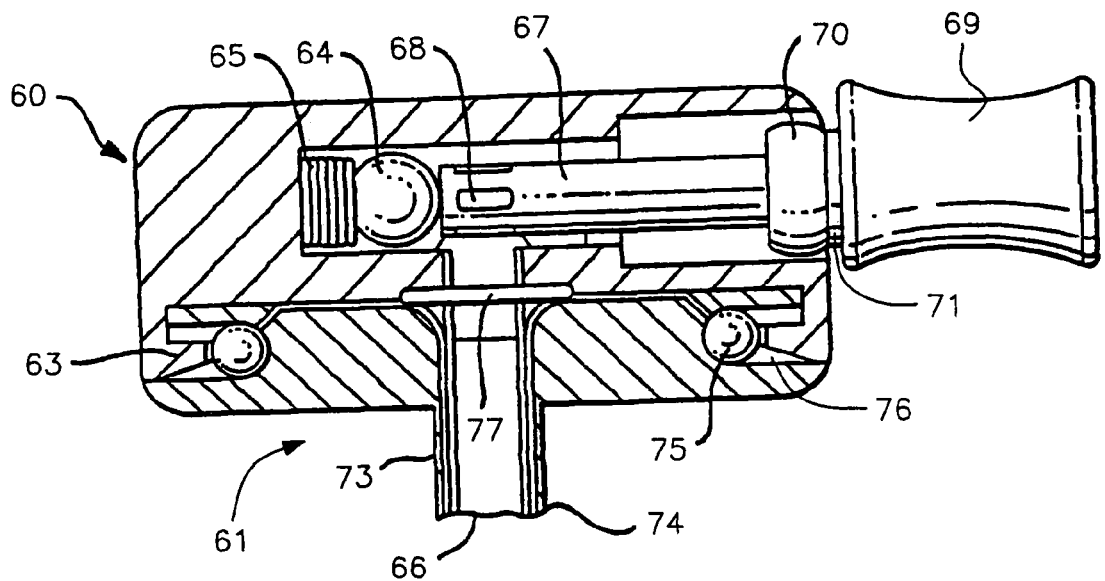
Figure 16:
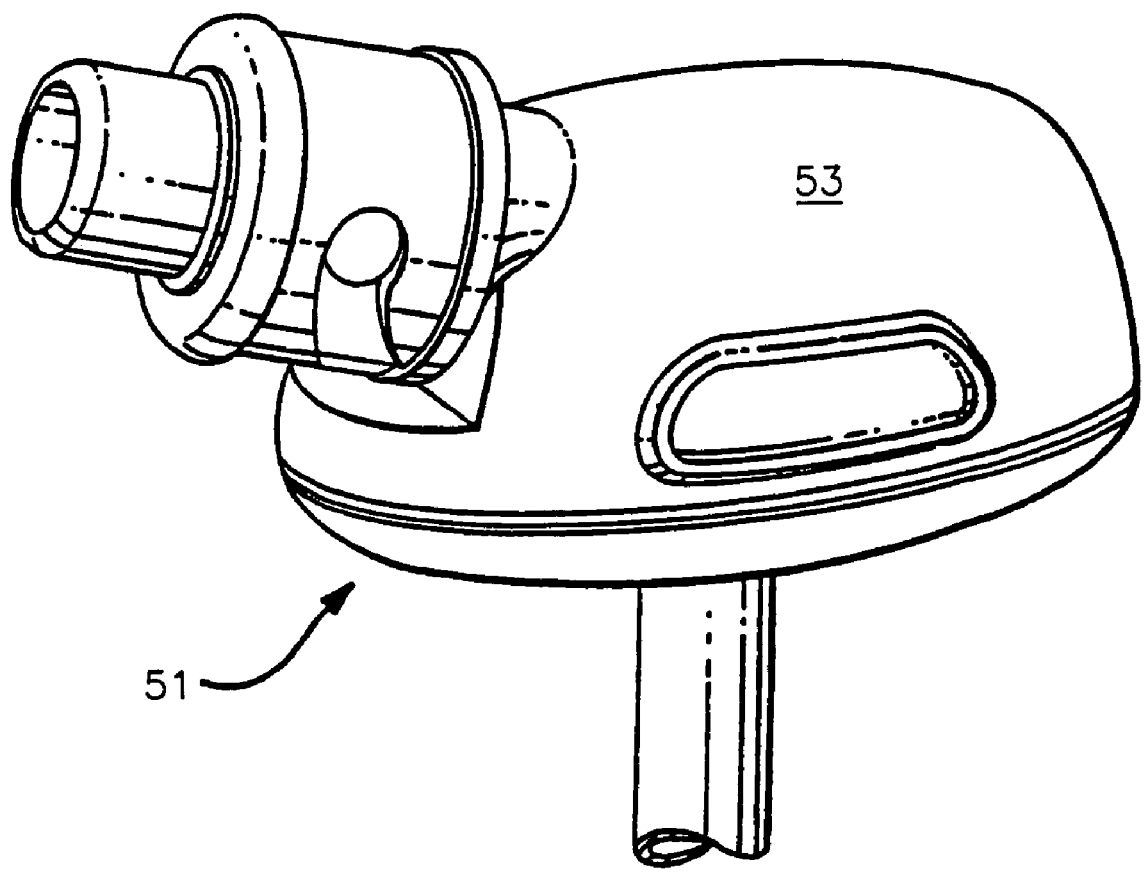

Referring now to FIGS. 15A and 15B, the set of parts 60 shown comprises the lumen element 61 and a valve member 62 in the form of a housing which is snap-engageable by resilient engagement members 63 in the form of a clip of the valve member and an undercut recess on the lumen element and releasable therefrom in a similar manner to that shown in FIGS. 14A to 14D by finger and thumb operable means (not shown).

The valve member 62 has a valve comprising a ball 64 mounted under pressure of a spring 65. The ball 64 seats in afrusto-conical valve part to close off a passage which when the valve member is mounted on the lumen element 61 is aligned with the lumen 66 of the lumen element (as shown in FIG. 15B) for flow of urine. The passage is opened by insertion of a catheter 67 so that the free end of the catheter pushes the ball 64 back against the force of the spring 65 and out of the valve seat to open the flow passage through the lumen 66 and the passage, fluid being able to pass into the catheter through entry bores or orifices 68 through the wall of the catheter 67. The catheter itself is received in a port and catheter connector 69 via a releasable clip mechanism 70, there being an 'O'-ring seal 71 to prevent leakage.

The lumen element 61 as in the previous embodiments has a retention means 72 for retaining the lumen element 61 in the body organ, such as a bladder of a patient.

In order to deploy the retention means 72, which is in the form of the cage shown, there are draw wires or strings 73, there being two, each of which is housed in a respective outer lumen 74 of the lumen element 61 and each of which is secured to a retention device in the embodiment in the form of a ball or sphere 75. The lumen element 61 has in its upper (as viewed) surface, a seat in the form of a cup or recess 76 for each ball 75. In operation, a surgeon or other medical practitioner grasps a ball 75 and pulls it upwardly, thereby drawing the wire or string 73 along the respective lumen 74. This action deploys the cage 72. To retain the cage 72 in the deployed condition, the wires or strings 73 are drawn up sufficiently to enable the balls 75 to be inserted in their respective seats 76, there being a groove for each we or string leading from its respective lumen 74 to the seat 76. When the valve 62 member is clipped into place, it holds the wires or strings 73 and the balls in place, so that the deployed state of the cage is safely and secured maintained.

There is an 'O'-ring seal 77 positioned at the top of the lumen 66 and under which the wires or strings 73 pass so as to prevent leakage of urine out of the lumen.

Referring now to FIGS. 16 to 27, there is shown therein a manufactured set of parts and an assembled device similar to the set and device schematically shown in FIGS. 14A to 14D, FIG. 16 being a general assembly of a medical device in the form of a suprapubic port 51 embodying the invention.

Figure 19:
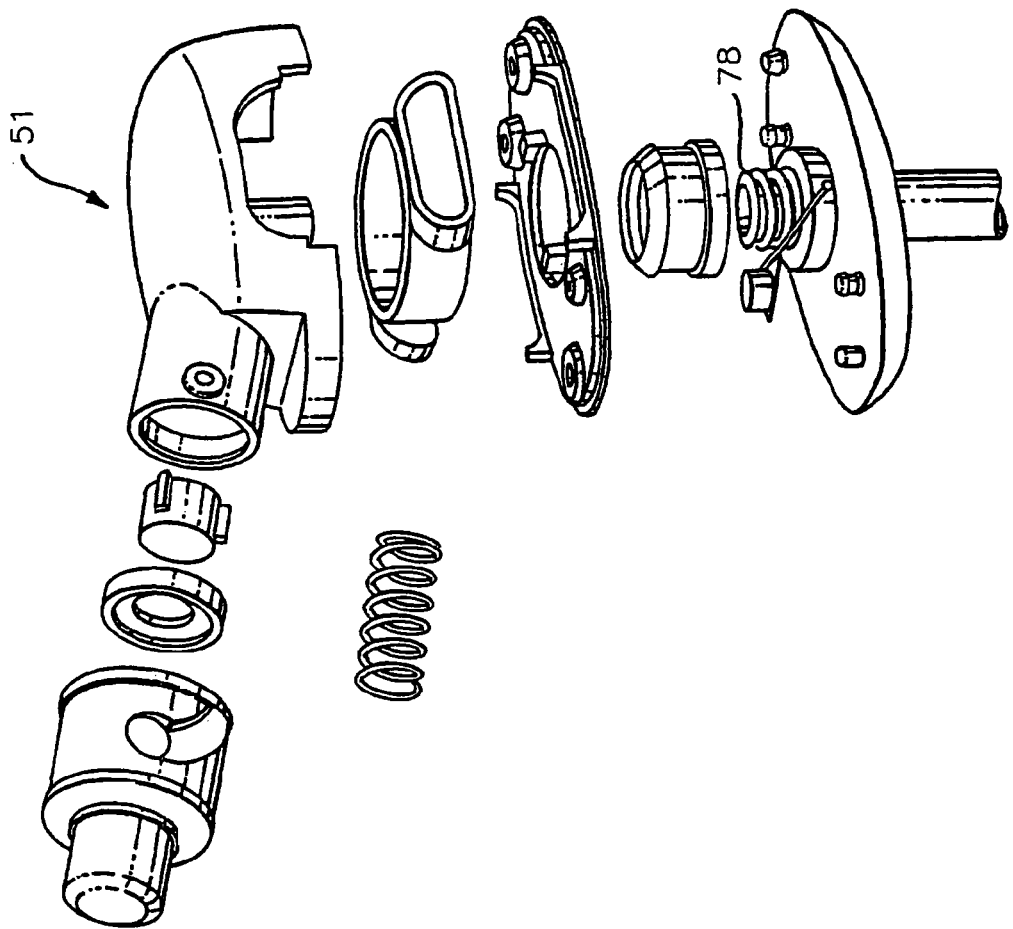
Figure 17:
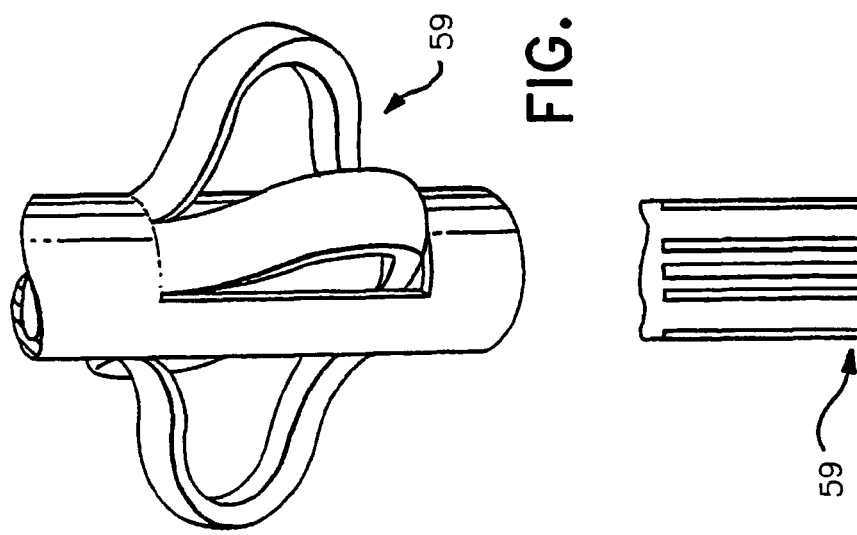
Figure 18:
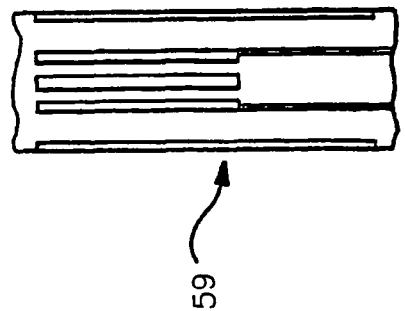
Figure 20:
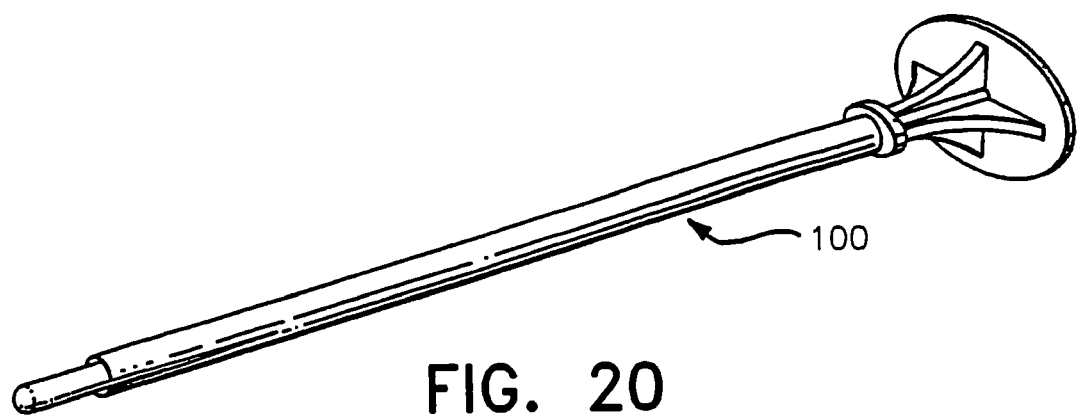
Figure 21:
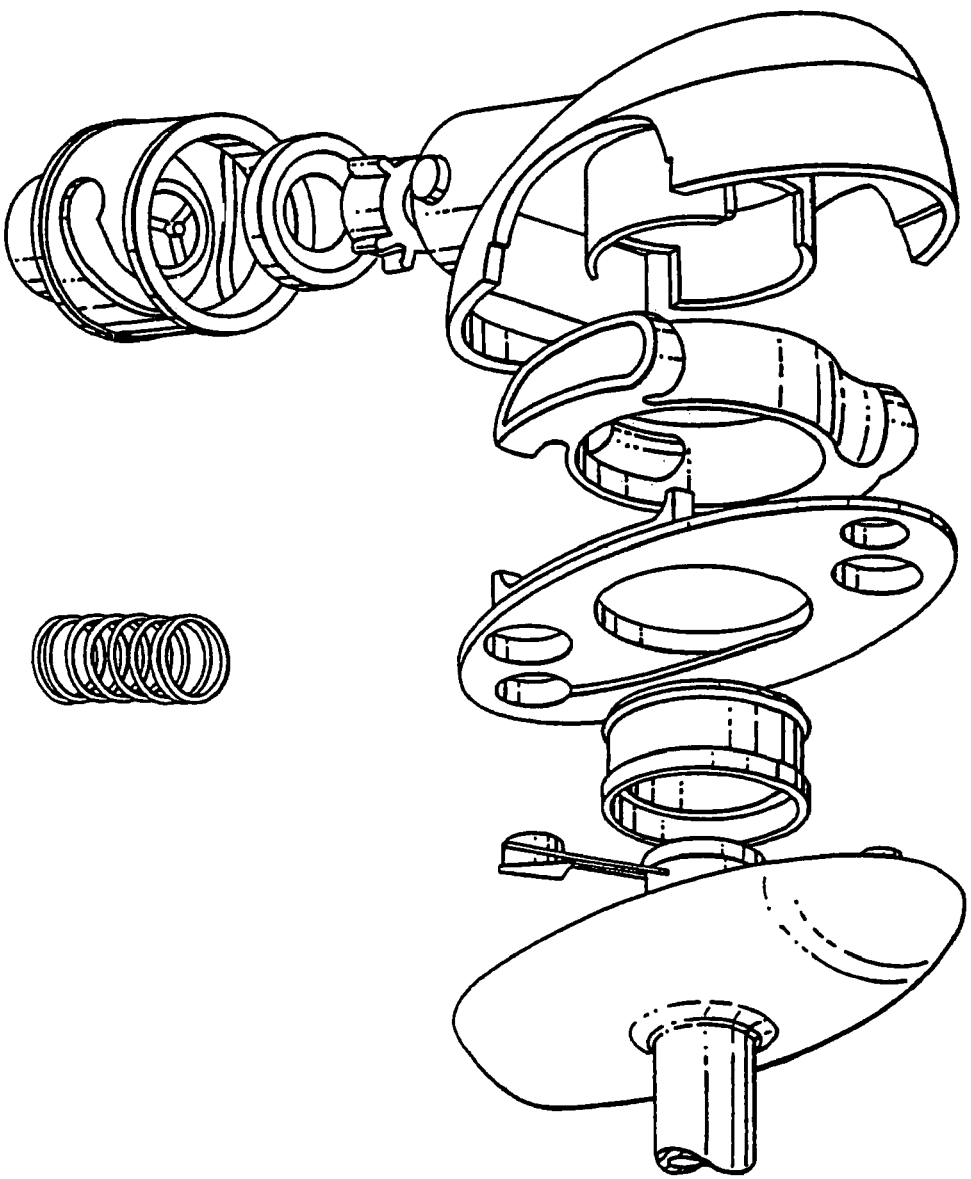
Figure 22:
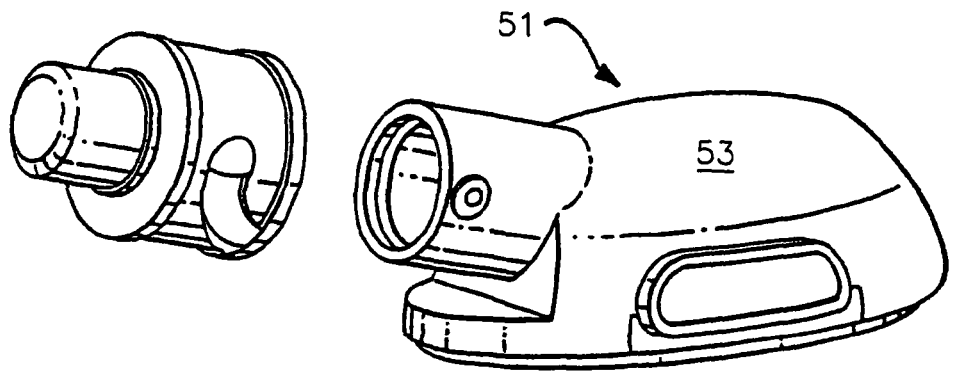
Figure 23:
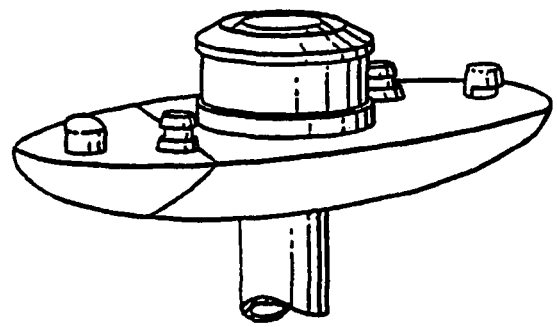
Figure 23:
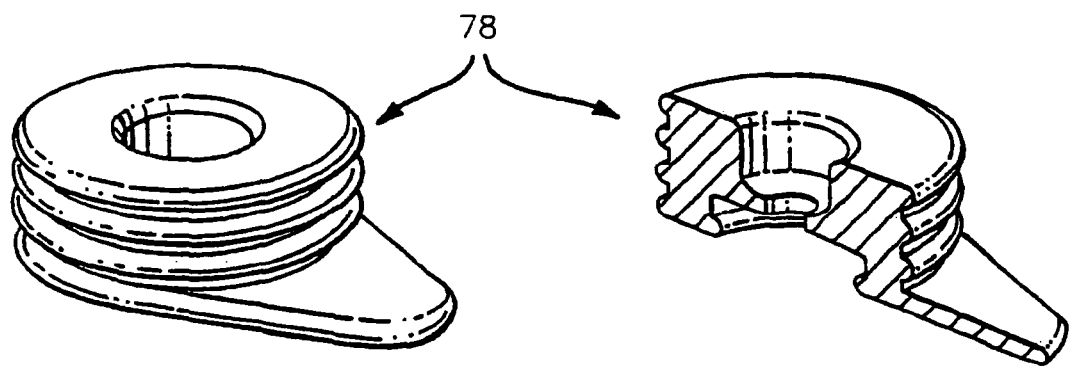
Figure 24:
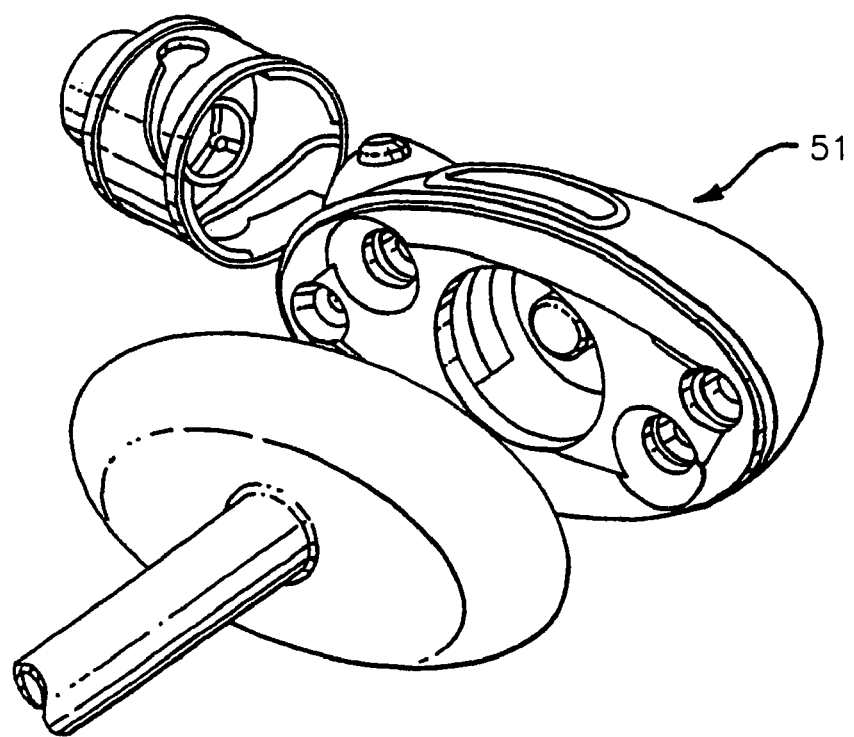
Figure 25:
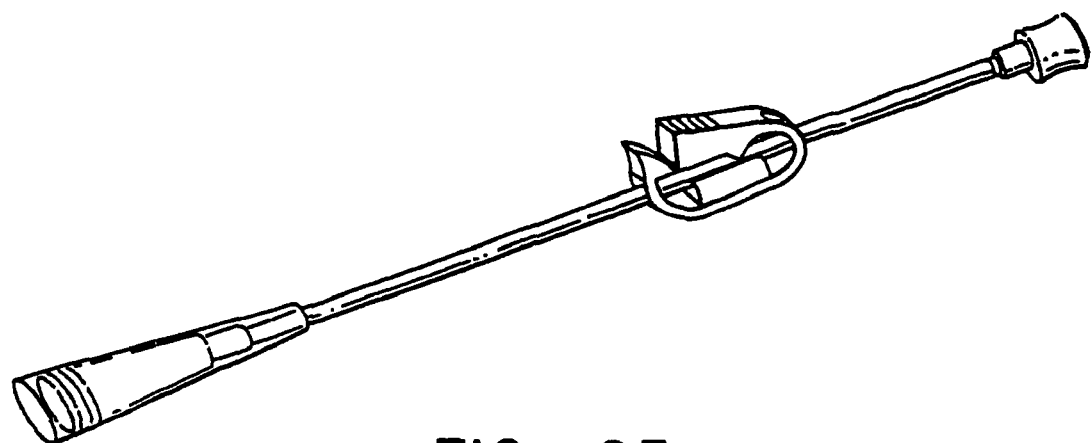

FIG. 17 shows a retaining device or lantern 59 in a deployed state for maintaining the assembled device in situ;

FIG. 18 showing the device 59 of FIG. 17 in an un-deployed state;

FIG. 19 shows an exploded view of the components of the suprapubic port 51;

FIG. 20 shows a perspective view of an insertion tool 100 which can be used to insert the suprapubic port 51 in a body;

FIG. 21 shows an exploded view of the port 51, from a reverse angle to that shown in FIG. 19;

FIG. 22 shows a general sub-assembly perspective view of the port 51;

FIG. 23 shows a perspective and longitudinal cross-sectional view of a seal 78;

FIG. 24 is a general sub-assembly view of the port 51 from below;

FIG. 25 shows a suprapubic port drainage tube;

FIG. 26 shows a perspective view of an irrigation tube with a plurality of lumen, in the FIG. two;

FIG. 27 shows an irrigation catheter housing, the bottom view being a longitudinal sectional view of the housing shown complete in the upper view.

In another embodiment, not shown, the valve member has a plurality (in the embodiment a pair) of bayonet connectors or lugs on the valve member housing and a cap which is secured as by screw engagement on the valve housing and onto the lugs. Inside the cap there is a concentric tube which bears on the valve as the cap is screwed over it. This tube seals against the valve and opens the valve mechanism, so in use allowing flow of urine out of the body via the lumen and lumen element.

Between 90° and 180° of turn is required to effect connection and screw the cap up tight. The cap has slots in its wall. In the tightened down condition the bayonet lugs are positioned to be adjacent the slots. If undue force is exerted on the drainage tube, the wall of the cap, weakened round the slots, flexes, and thereby allows the lugs to pop out, thereby releasing the connector.

It will be understood that the disconnection force will be determined by choice of material of the cap and by parameters such as wall thickness and the depth of the slots. Also, the slots may be replaced by zones of weakness, namely a thinned section or web thinner than the remaining cap wall thickness, rather than through slots. Also, the cap material is such as to allow flexing without damage to the cap or to the bayonet lugs, so allowing re-use and re-connection once the cause of disconnection has been removed.

In all embodiments, the set of parts provides a urine drainage system which is easy to connect and disconnect, and which stays connected unless intentionally disconnected, or when subject to strain as described above, for example from a dropped urine bag or by the tubing becoming snagged.

In all embodiments the various parts of the set are manufactured from suitable materials, for example polymeric materials, metal such as produced by powder metallurgical processes, or a combination of suitable materials.

The embodiments described with reference to the drawings provide a care regime for a long-term catheterised (urinary) incontinent patient via a suprapubic support (the lumen element) and associated devices, which support is essentially implanted in the patient.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A set of parts for providing a urine drainage system configured to form a fluid passageway through an external skin surface and into a bladder to permit drainage of the bladder, the system comprising:

a lumen element having a proximal end portion and a distal end portion with an elongated depending lumen disposed between the distal end portion and the proximal end portion so as to form a drainage lumen, a retention element coupled with the distal end portion and configured for adjustment between a first position selected for insertion and a second position selected for retention, a lumen housing forming the proximal end portion and having a distal face configured to abut the external tissue surface adjacent to the tissue through which the depending lumen is passed and a proximal face through which a terminus of the depending lumen is formed, the lumen housing further including a first connection member, wherein the lumen element and lumen housing are formed from a single, unitary continuous component that presents an unimpeded passage from an opening in the proximal face through the lumen element;

a valve housing having a first opening forming a port and catheter connector, a second opening, a fluid passageway disposed between the first opening and the second opening, a valve member disposed within the fluid passageway and configured to selectively occlude fluid flow through the fluid passageway, and a second connection member configured to selectively engage the first connection member such that a seal is formed between the valve housing and the lumen element and the second opening of the valve housing is operatively placed in fluid communication with the depending lumen when the valve housing abuts the proximal face of the lumen housing and wherein both the first opening and the valve member are disposed proximal to the proximal face of the lumen housing;

a urinary catheter having a free end configured for insertion into the port and catheter connector in the valve housing to actuate the valve member to open the fluid passageway and to permit fluid flow from the distal end portion of the lumen element, through the drainage lumen, into the second opening of the valve housing, then into the free end of the urinary catheter and out through the urinary catheter.

2. The set of parts according to claim 1, wherein the lumen element is configured as an implant.

3. The set of parts according to claim 1, wherein the valve member is a ball valve having a valve ball.

4. The set of parts according to claim 3, wherein the ball valve is biased by a spring.

5. The set of parts according to claim 3, wherein the valve member has a housing including a spherical valve seat.

6. The set of parts according to claim 3, wherein the valve member has a housing including a frusto-conical valve seat for the valve ball.

7. The set of parts according to claim 4, wherein the valve member has a housing including a frusto-conical valve seat for the valve ball.

8. The set of parts according to claim 1, wherein the catheter further comprises an O-ring seal against the valve member.

9. The set of parts according to claim 1, wherein said releasable connection members are configured to engage one another with a snap fit.

10. The set of parts according to claim 1, wherein said retention element having an insertion position in which, during entry of the lumen element into the bladder from the patient's skin through a lumen-sized hole, the retention element also passes through the patient's skin and into the bladder through said same lumen-sized hole, said retention element once inserted being expandable into a deployed position having a diameter greater than said lumen-sized hole to retain the lumen element in the bladder.

11. A kit with a set of parts for providing a urine drainage system, comprising:
a lumen element including a housing forming a proximal end of the lumen element and a lumen for drainage of urine, said lumen element being configured to be mounted for entry into the body of a patient from the patient's skin and the housing abuts the patient's skin to retain the position of the lumen element, said lumen element housing having a first connection member spaced from an inner surface of said lumen, wherein the lumen element and lumen housing are formed from a single, unitary continuous component that presents an unimpeded passage from an opening in the proximal face through the lumen element;
a valve housing having a fluid passage that is selectively coupleable with the lumen and includes a valve member disposed within the fluid passageway, said valve member being movable to open and close said fluid passageway, said valve housing having a second connection member configured to cooperatively engage with said first connection member on said lumen element housing;
a urinary catheter having a free end that is received in the valve member housing, said catheter when inserted therein pushing against the valve member to open said fluid passageway but wherein the valve member precludes insertion of the catheter distal to the proximal end of the lumen element;
said lumen element housing and said valve member housing being releasably connected to one another by said first and second connection members which can be engaged with and disengaged from one another by hand to releasably connect and disconnect said lumen element and said valve member, said lumen communicating with said fluid passage when said housings are connected such that an assembled medical device is provided which is configured to drain the patient's bladder by having urine flow through the lumen, into the valve, then into the free end of said catheter, and then out through the catheter.

12. The kit according to claim 11, wherein the lumen element is configured as an implant.

13. The kit according to claim 11, further comprising a retaining element adapted to retain the lumen element in the bladder.

14. The kit according to claim 11, wherein the valve member is a ball valve having a valve ball.

15. The kit according to claim 14, wherein the ball valve is biased by a spring which is compressed by the free end of the catheter when the catheter is inserted in the valve member housing.

16. The kit according to claim 14, wherein the valve member has a housing including a spherical valve seat.

17. The kit according to claim 14, wherein the valve member has a housing including a frusto-conical valve seat for the valve ball.

18. The kit according to claim 15, wherein the valve member has a housing including a frusto-conical valve seat for the valve ball.

19. The kit according to claim 11, wherein the catheter further comprises an O-ring seal against the valve member.

20. The kit according to claim 13, wherein said retaining element includes a pull element which extends along said lumen and is secured to said lumen element housing by a retention device.

21. The kit according to claim 20, wherein said retention device includes a spherical member seated in a recess of said lumen element housing.

22. The kit according to claim 11, wherein said hand-operable connection members are configured to engage one another with a snap fit.

23. The kit according to claim 11, further comprising a retaining element having an insertion position in which, during entry of the lumen element into the bladder from the patient's skin through a lumen-sized hole, the retaining element also passes through the patient's skin and into the bladder through said same lumen-sized hole, said retaining element once inserted being expandable into a deployed position having a diameter greater than said lumen-sized hole to retain the lumen element in the bladder.

* * * * *